US006602685B1

(12) United States Patent
Lohse (10) Patent No.: US 6,602,685 B1
(45) Date of Patent: Aug. 5, 2003

(54) IDENTIFICATION OF COMPOUND-PROTEIN INTERACTIONS USING LIBRARIES OF PROTEIN-NUCLEIC ACID FUSION MOLECULES

(75) Inventor: Peter Lohse, Weston, MA (US)

(73) Assignee: Phylos, Inc., Lexington, MA (US)

( * ) Notice: Subject to any disclaimer, the term of this patent is extended or adjusted under 35 U.S.C. 154(b) by 0 days.

(21) Appl. No.: 09/374,964

(22) Filed: Aug. 16, 1999

Related U.S. Application Data

(60) Provisional application No. 60/096,820, filed on Aug. 17, 1998.

(51) Int. Cl.[7] .............................. C12P 21/06; C12Q 1/68; G01N 33/543
(52) U.S. Cl. ...................... 435/69.1; 435/6; 435/68.1; 435/69.7; 436/518; 424/134.1
(58) Field of Search .................... 435/6, 68.1; 436/518; 424/134.1

(56) References Cited

U.S. PATENT DOCUMENTS

| 4,537,861 A | * | 8/1985 | Elings et al. ............... 436/518 |
| 4,587,044 A | | 5/1986 | Miller et al. |
| 5,223,409 A | | 6/1993 | Ladner et al. |

(List continued on next page.)

FOREIGN PATENT DOCUMENTS

| DE | 19646372 | 11/1996 |
| WO | WO 93/03172 | 2/1983 |
| WO | WO 91/05058 | 4/1991 |
| WO | WO 92/00091 | 1/1992 |
| WO | WO 92/02536 | 2/1992 |
| WO | WO 92/18645 | 10/1992 |
| WO | WO 95/11922 | 5/1995 |
| WO | WO 95/32425 | 11/1995 |
| WO | WO 96/22391 | 7/1996 |
| WO | WO 98/16636 | 4/1998 |
| WO | WO 98/37186 | 8/1998 |
| WO | WO 98/58080 | 12/1998 |

OTHER PUBLICATIONS

Niemeyer et al., "Oligonucleotide–Directed Self–Assembly of Proteins: Semisynthetic DNA—Streptavidin Hybrid Molecules as Connectors for the Generation of Macroscopic Arrays and the Construction of Supramolecular Bioconjugates," Nucl. Acid Res. 22:5530–5539 (1994).

Abelson, "Directed Evolution of Nucleic Acids by Independent Replication and Selection," *Science* 249:488–489 (1990).

Barrett et al., "A Monoclonal Antibody Specific for a Dynorphin Precursor," *Neuropeptides* 6:113–120 (1985).

Botstein et al., "Strategies and Applications of in Vitro Mutagenesis," *Science* 229:1193–1201 (1985).

(List continued on next page.)

*Primary Examiner*—Marianne P. Allen
*Assistant Examiner*—Lori A. Clow
(74) *Attorney, Agent, or Firm*—Clark & Elbing LLP (57) ABSTRACT

Disclosed herein is a method for detecting a compound-protein interaction, involving: (a) providing a compound library in which each member of the compound library is immobilized on a solid support; (b) contacting each member of the immobilized compound library in a single reaction chamber with each member of a protein-nucleic acid fusion library under conditions which allow the formation of compound-fusion complexes; (c) isolating the immobilized compound-fusion complexes; and (d) detecting a compound-fusion complex as an indication that the protein of the fusion interacts with the compound. In preferred embodiments, the protein is identified by reading the nucleic acid portion of the fusion, and the compound is identified by reading a detectable tag bound to either the compound or the solid support.

32 Claims, 4 Drawing Sheets

U.S. PATENT DOCUMENTS

| | | | |
|---|---|---|---|
| 5,264,563 A | | 11/1993 | Huse |
| 5,270,163 A | | 12/1993 | Gold et al. |
| 5,270,170 A | | 12/1993 | Schatz et al. |
| 5,424,186 A | | 6/1995 | Fodor et al. |
| 5,432,018 A | | 7/1995 | Dower et al. |
| 5,498,530 A | | 3/1996 | Schatz et al. |
| 5,541,061 A | | 7/1996 | Fodor et al. |
| 5,565,324 A | | 10/1996 | Still et al. |
| 5,605,793 A | | 2/1997 | Stemmer |
| 5,627,024 A | | 5/1997 | Maruyama et al. |
| 5,639,603 A | | 6/1997 | Dower et al. |
| 5,643,768 A | | 7/1997 | Kawasaki |
| 5,658,754 A | | 8/1997 | Kawasaki |
| 5,723,323 A | | 3/1998 | Kauffman et al. |
| 5,733,731 A | | 3/1998 | Schatz et al. |
| 5,751,629 A | | 5/1998 | Nova et al. |
| 5,763,263 A | * | 6/1998 | Dehlinger .................. 435/287 |
| 5,770,455 A | | 6/1998 | Cargill et al. |
| 5,789,208 A | | 8/1998 | Sharon |
| 5,795,747 A | | 8/1998 | Henco et al. |
| 5,843,701 A | * | 12/1998 | Gold et al. ................ 435/68.1 |
| 5,849,878 A | | 12/1998 | Cantor et al. |
| 5,872,015 A | * | 2/1999 | Venton et al. .............. 436/538 |
| 5,962,645 A | * | 10/1999 | Keay et al. ................. 530/350 |
| 5,965,133 A | | 10/1999 | Cantor et al. |
| 5,985,575 A | | 11/1999 | Wickens et al. |
| 6,046,056 A | * | 4/2000 | Parce et al. ................. 204/400 |
| 6,100,026 A | * | 8/2000 | Nova et al. ..................... 435/6 |
| 6,207,446 B1 | * | 3/2001 | Szostak et al. .......... 435/287.2 |

OTHER PUBLICATIONS

Bujard et al., "[26] A T5 Promoter–Based Transcription–Translation System for the Analysis of Proteins in Vitro and in Vivo," *Methods in Enzymology* 155:416–433 (1987).

Clackson et al., "In Vitro Selection from Protein and Peptide Libraries," *Tibtech* 12:173–184 (1994).

Cwirla et al., "Peptides on Phage: A Vast Library of Peptides for Identifying Ligands," *Proc. Natl. Acad. Sci.* 87:6378–6382 (1990).

Devlin et al., "Random Peptide Libraries: A Source of Specific Protein Binding Molecules," *Science* 249:404–406 (1990).

Eigen et al., "Molecular Quasi–Species," *Journal of Physical Chemistry* 92:6881–6891 (1988).

Eigen et al., "The Hypercycle. Coupling of RNA and Protein Biosynthesis in the Infection Cycle of an RNA Bacteriophage," *Biochemistry* 30:11005–11018 (1991).

Eigen, "Viral Quasispecies," *Scientific American* 269:32–39 (1993).

Eigen, "New Concepts for Dealing with the Evolution of Nucleic Acids," *Cold Spring Harb. Symp. Quant. Biol.* 52:307–320 (1987).

Eigen et al., "Evolutionary Molecular Engineering Based on RNA Replication," *Pure & Appl. Chem.* 56(8):967–978 (1984).

Gersuk et al., "High–Affinity Peptide Ligands to Prostate–Specific Antigen Identified by Polysome Selection," *Biochem. Biophys. Res. Commun.* 232(2):578–582 (1997).

Geysen et al., "Use of Peptide Synthesis to Probe Viral Antigens for Epitopes to a Resolution of a Single Amino Acid," *Proc. Natl. Acad. Sci.* 81:3998–4002 (1984).

Guatelli et al., "Isothermal, in vitro Amplification of Nucleic Acids by a Multienzyme Reaction Modeled after Retroviral Replication," *Proc. Natl. Acad. Sci.* 87:1874–1878 (1990).

Higuchi, "Using PCR to Engineer DNA," *Stockton Press* 61–70 (1989).

Horwitz et al., "Selection of New Biological Activities from Random Nucleotide Sequences: Evolutionary and Practical Considerations," *Genome* 31:112–117 (1989).

Hui et al., "Mutagenesis of the Three Bases Preceding the Start Codon of the B–galactosidase mRNA and its Effect on Translation in *Escherichia coli*," *The EMBO Journal* 3:623–629 (1984).

Hunkapiller et al., "A Microchemical Facility for the Analysis and Synthesis of Genes and Proteins," *Nature* 310:105–111 (1984).

Jamieson et al., "In Vitro Selection of Zinc Fingers with Altered DNA–Binding Specificity," *Biochemistry* 33:5689–5695 (1994).

Kraus et al., "Purification of Low–Abundance Messenger RNAs from Rat Liver by Polysome Immunoadsorption," *Proc. Natl. Acad. Sci.* 79:4015–4019 (1982).

Thiesen and Bach, Nuc. Acids Res. 18:3203–3209 (1990).

Bartel et al., Cell 67:529–536 (1991).

Stormo and Yoshioka, Proc. Natl. Acad. Sci. USA 88:5699–5703 (1991).

Bock et al., Nature 355:564–566 (1992).

Green et al., Nature 347:406–408 (1990).

Robertson and Joyce, Nature 344:467–468 (1990).

Beudry and Joyce, Science 257:635–641 (1992).

Bartel and Szostak, Science 261:1411–1418 (1993).

Lorsch and Szostak, Nature 371:31–36 (1994).

Cuenoud and Szostak, Nature 375:611–614 (1995).

Chapman and Szostak, Chemistry and Biology 2:325–333 (1995).

Lohse and Szostak, Nature 381:442–444 (1996).

Ellman et al., Meth. Enzymol. 202:301–336 (1991).

Milstein, Sci. Amer. 243:66–74 (1980).

Smith, Science 228:1315–1317 (1985).

Parmley and Smith, Gene 73:305–318 (1988).

McCafferty et al., Nature 348:552–554 (1990).

Cull et al., Proc. Natl. Acad. Sci. USA 89:1865–1869 (1992).

Korman et al., Proc. Natl. Acad. Sci. USA 79:1844–1848 (1982).

Mattheakis et al., Proc. Natl. Acad. Sci. USA 91:9022–9026 (1994).

Mattheakis et al., Meth. Enzymol. 267:195–205 (1996).

Hanes and Pluckthun, Proc. Natl. Acad. Sci. USA 94:4937–4942 (1997).

Brenner and Pluckthun, Proc. Natl. Acad. Sci. USA 89:5381–5383 (1992).

Traut and Monro, J. Mol. Biol. 10:63–72 (1964).

Smith et al., J. Mol. Biol. 13:617–628 (1965).

Ekland et al., Nucl. Acids Research 23:3231–3238 (1995).

Stemmer, Nature 370: 389–391 (1994).

Fraser and Rich, Proc. Natl. Acad. Sci. USA 70:2671–2675 (1973).

Krayevsky and Kukhanova, Progress in Nucleic Acids Research and Molecular Biology 23:1–51 (1979).

Roberts and Szostak, Proc. Natl. Acad. Sci. USA 94:12297–12302 (1997).

Roberts, "In Vitro selection of proteins vis RNA–proteins fusions," FY 95, Abstract.

Roberts, "In Vitro selection of proteins via RNA–proteins fusions," FY 96, Abstract.

Needels et al., "Generation and Screening of an Oligonucleotide–Encoded Synthetic Peptide Library," Proc. Natl. Acad. Sci. USA 90:10700–10704 (1993).

Husimi et al., "Role of the Virus–Type Strategy in Encoded Molecular Evolution," Progress in Biophysics and Molecular Biology, vol. 65 (Supp. 1), Abstract P–A5–04 (1996).

* cited by examiner

IDENTIFICATION OF COMPOUND-PROTEIN INTERACTIONS USING LIBRARIES OF PROTEIN-NUCLEIC ACID FUSION MOLECULES

CROSS REFERENCE TO RELATED APPLICATIONS

This application claims the benefit of the filing date of co-pending Prov. application, U.S. Ser. No. 60/096,820, filed Aug. 17, 1998.

BACKGROUND OF THE INVENTION

In general, the invention features screening methods involving nucleic acid-protein fusions.

Screening is considered to be an efficient tool to identify binding interactions between proteins and small molecule compounds derived from large pharmaceutically-based collections, new synthetic approaches such as combinatorial chemistry, or natural sources (TIBTECH, vol. 13, p. 115, 1995). However, the multidisciplinary nature of most screening techniques poses significant challenges. The most important challenge of such techniques is maintaining a ready supply of materials for the screen. Screening of small compound libraries with different protein targets requires sufficient amounts of compound. Alternatively, screening of large compound libraries (for example, having $10^6$ members or greater) requires large amounts of recombinant protein. Another challenge is to operate the screen rapidly and cost effectively. Screening of compound libraries with different protein targets is generally time consuming if carried out in a sequential fashion.

Lately, a method has been described for the isolation of proteins with desired properties out of a pool of proteins (Szostak et al., Selection of Proteins Using RNA-Protein Fusions, U.S. Ser. No. 09/007,005, Jan. 14, 1998, now U.S. Pat. No. 6,258,558 B1, and U.S. Ser. No. 09/247,190, Feb. 9, 1999, now U.S. Pat. No. 6,261,804 B1; and Roberts & Szostak, Proc. Natl. Acad. Sci. USA (1997) vol. 94, p. 12297–12302). This technique is accomplished by means of protein-RNA fusion molecules where each protein is covalently linked to its encoding RNA. The protein-RNA fusion technology may be used to screen cDNA libraries and to clone new genes on the basis of protein-protein interactions (see, for example, Szostak et al., Selection of Proteins Using RNA-Protein Fusions, U.S. Ser. No. 09/007,005, Jan. 14, 1998, now U.S. Pat. No. 6,258,558 B1, and U.S. Ser. No. 09/247,190, Feb. 9, 1999, now U.S. Pat. No. 6,261,804 B1).

SUMMARY OF THE INVENTION

The purpose of the present invention is to efficiently identify protein-compound binding interactions (and, particularly, protein-small molecule interactions) by screening small molecule compounds with libraries of protein-nucleic acid fusions (for example, protein-RNA fusions) in a parallel fashion, thus providing a catalogue of small molecule-protein pairs.

Accordingly, in a first aspect, the invention features a method for detecting a compound-protein interaction, the method involving: (a) providing a compound library in which each member of the compound library is immobilized on a solid support; (b) contacting each member of the immobilized compound library in a single reaction chamber with each member of a protein-nucleic acid fusion library under conditions which allow the formation of compound-fusion complexes; (c) isolating the immobilized compound-fusion complexes; and (d) detecting the compound-fusion complex as an indication that the protein of the fusion interacts with the compound.

In preferred embodiments, the protein-nucleic acid fusion is either a protein-RNA fusion, a protein-DNA fusion, or a protein fused to a DNA-RNA hybrid; the solid support is a bead; each bead is coded with a unique detectable label; the compound of the complexed protein-nucleic acid fusion is identified by the unique detectable label associated with the bead; the detectable label is a peptide label, a nucleic acid label, a chemical label, a fluorescent label, or a radio frequency tag; the solid support is a chip and the compound library is immobilized on the chip in an addressable array; each member of the protein-nucleic acid fusion library is detectably labeled; the compound-fusion complex, or the components thereof, are recovered by release from the solid support; the method further involves recovering the protein-nucleic acid fusion from the solid support and identifying the protein; the identity of the protein is determined from the sequence of the nucleic acid portion of the protein-nucleic acid fusion; and the compound is a small molecule.

In a related aspect, the invention features a method for detecting a compound-protein interaction, the method involving: (a) providing a compound immobilized on a solid support; (b) contacting the immobilized compound with a protein-nucleic acid fusion library under conditions which allow the fusion to bind to the compound; and (c) detecting a bound protein-nucleic acid fusion as an indication that the protein of the protein-nucleic acid fusion interacts with the compound.

In preferred embodiments, the protein-nucleic acid fusion is either a protein-RNA fusion, a protein-DNA fusion, or a protein fused to a DNA-RNA hybrid; the protein-nucleic acid fusion is detectably labeled and the interaction is indicated by the association of the detectable label with the solid support; the bound protein-nucleic acid fusion is recovered by release from the solid support; the method further involves recovering the protein-nucleic acid fusion from the solid support and identifying the protein; the identity of the protein is determined from the sequence of the nucleic acid portion of the protein-nucleic acid fusion; the solid support is a column, glass slide, chip, or bead; and the compound is a small molecule.

As used herein, by a "library" is meant a collection of at least two molecules (for example, molecules such as compounds or protein-nucleic acid fusions). A compound library preferably includes at least $10^2$ or $10^3$ members, and, more preferably, at least $10^4$, $10^5$, or $10^6$ members. A protein-nucleic acid library (for example, a protein-RNA library) preferably includes at least $10^2$ or $10^3$ members, more preferably, at least $10^4$, $10^5$, or $10^6$ members, and, most preferably, at least $10^{10}$ or $10^{12}$ members.

By a "DNA-RNA hybrid" is meant a DNA strand hybridized to a complementary RNA strand. Typically, the DNA strand is generated by reverse transcription of the RNA molecule.

By "addressable array" is meant a fixed pattern of immobilized objects on a solid surface in which the identity of the objects is known or can be readily determined.

By a "small molecule" is meant a compound with a molecular weight of less than or equal to 10,000 Daltons, preferably, less than or equal to 1000 Daltons, and, most preferably, less than or equal to 500 Daltons.

The present invention provides a number of advantages. For example, the present methods reduce the amount of material required for a screen. In standard screens, considerable amounts of protein and small molecule compounds are required because each compound is screened with a single protein in a spatially segregated chamber. A library of protein-nucleic acid fusion molecules, however, can be screened for binding interactions with small molecule compounds in the same reaction chamber in a parallel fashion. In addition, the protein target need not be cloned, overexpressed, or isolated, but rather is screened as a protein-nucleic acid fusion molecule and identified by its coding nucleic acid. Moreover, material costs may be further reduced by miniaturization, which is facilitated by the present methods and is limited solely by the choice of detection method for the identification of small molecule-fusion complexes.

In addition, the present invention provides advantages in terms of the time required to carry out a compound screen. In particular, the methods described herein accelerate the identification of ligands (for example, small molecule ligands) by screening a library of protein targets with a library of potential ligands in a parallel fashion. In contrast to standard screens, where a small compound library is screened for binding to different proteins in a sequential fashion, small molecule compounds may be screened, in the present techniques, with a library of protein-nucleic acid fusions in a single assay. Consequently, the present invention facilitates the screening of members of a library of small molecule compounds for binding to the members of a library of proteins in a highly efficient manner.

Other features and advantages of the invention will be apparent from the following detailed description, and from the claims.

DETAILED DESCRIPTION

The methods of the present invention facilitate the efficient identification of protein-compound (and, preferably, protein-small molecule) binding interactions by screening such compounds with libraries of protein-nucleic acid fusions (for example, protein-RNA fusions), thus providing a catalog of compound-protein pairs. If desired, libraries of compounds may be screened against libraries of protein-nucleic acid fusions in a single screen. In preferred embodiments, either the compounds or the fusions are immobilized on a solid support (for example, a bead, chip, glass slide, or column) to simplify the screen and/or result readings. In addition, to facilitate the identification of compound-protein pairs, the compound (or the solid support to which it is immobilized) may be tagged with a detectable label characteristic of that particular compound or compound family.

Any compound may be screened by the methods of the invention, although small molecules represent preferred targets for screening.

These and other aspects of the invention are now described in more detail below. These examples are provided for the purpose of illustrating the invention, and should not be construed as limiting.

Screening Assays

Figure 1:
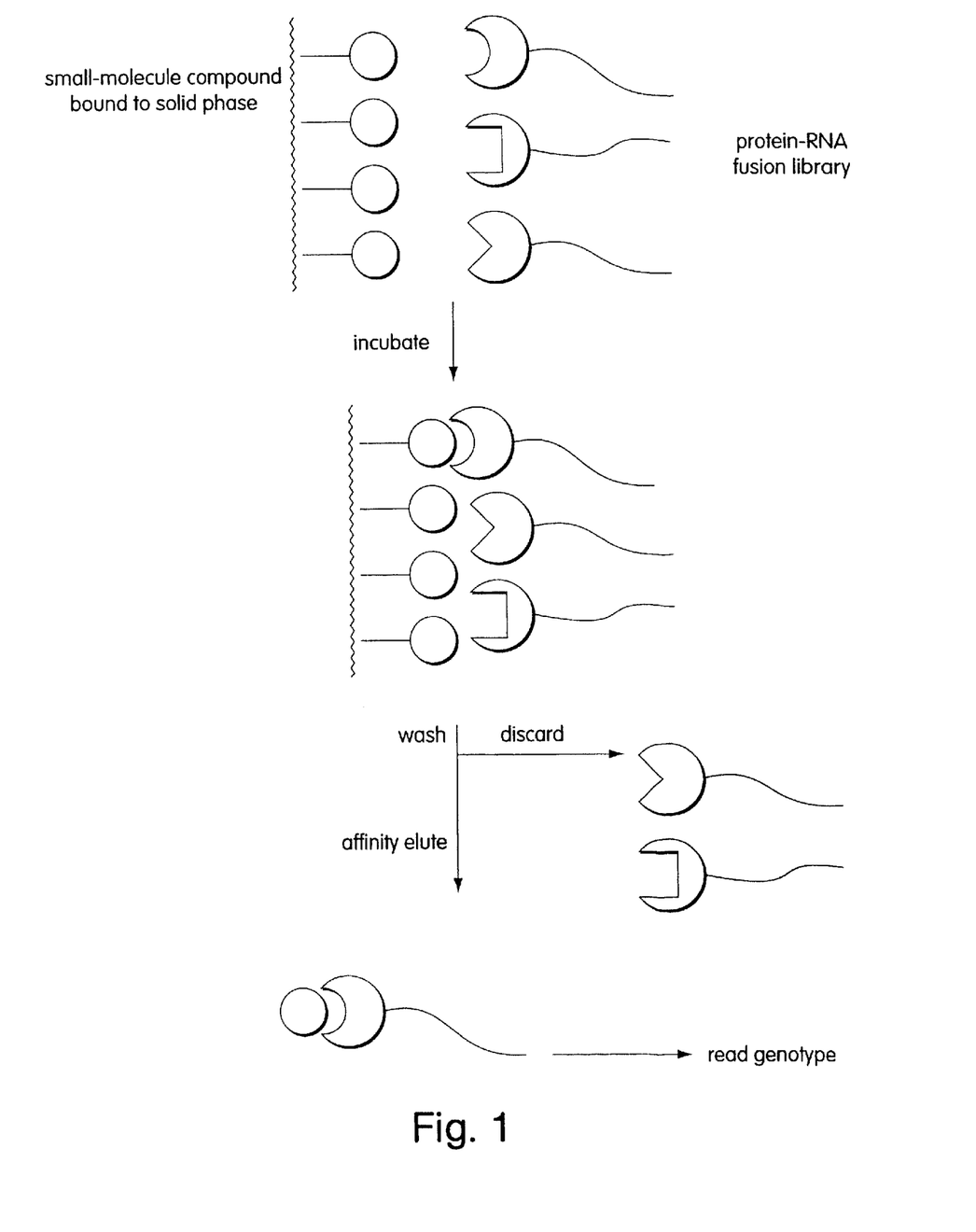
FIG. 1 is a schematic illustration of an exemplary approach to screening a compound immobilized on a solid support with a library of protein-nucleic acid fusions.

As discussed above, screening of compounds against protein-nucleic acid fusions (for example, protein-RNA fusions) may be carried out in a number of different formats. One particular format is illustrated in FIG. 1. By this approach, a single compound is immobilized on a column or any other solid surface using any one of a variety of standard methods. The solid phase-bound small molecule compound is then incubated with screening buffer containing BSA or another inert protein to reduce non-specific binding. Next, the buffer solution is removed, and the solid phase presenting the compound is incubated with a solution of a protein-nucleic acid fusion library, followed by washes with screening buffer to remove non-specifically bound fusion molecules. Specifically bound protein-nucleic acid fusions are then eluted (for example, by affinity elution using buffer containing free small molecule compound). "Reading" the nucleic acid (for example, RNA) portion of the eluted fusion molecules provides an identification of the protein that bound the small molecule compound. Such a "reading" may be carried out as described below.

Figure 2:
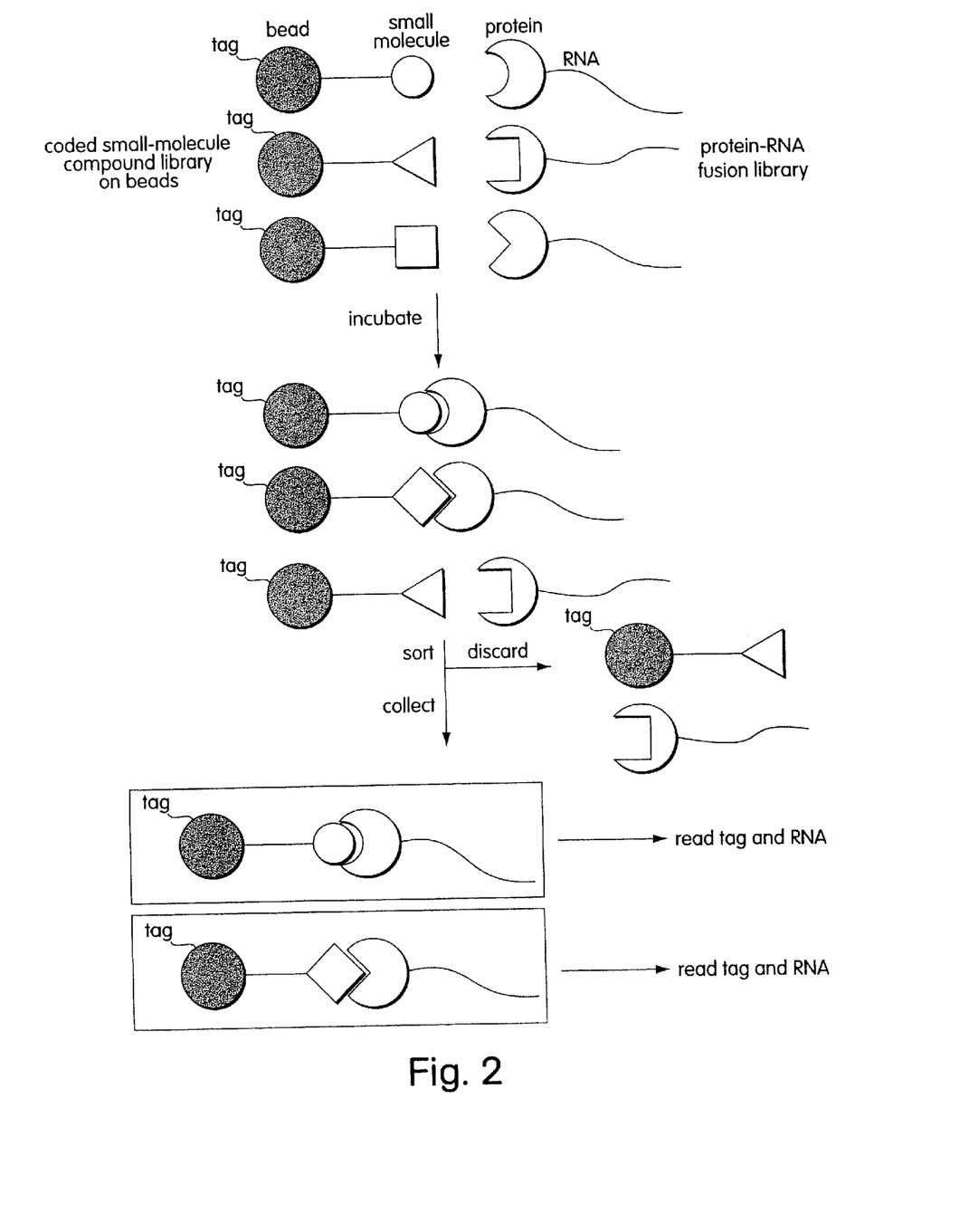
FIG. 2 is a schematic illustration of an exemplary approach to screening a library of compounds immobilized to beads with a library of protein-nucleic acid fusions.
Figure 3:
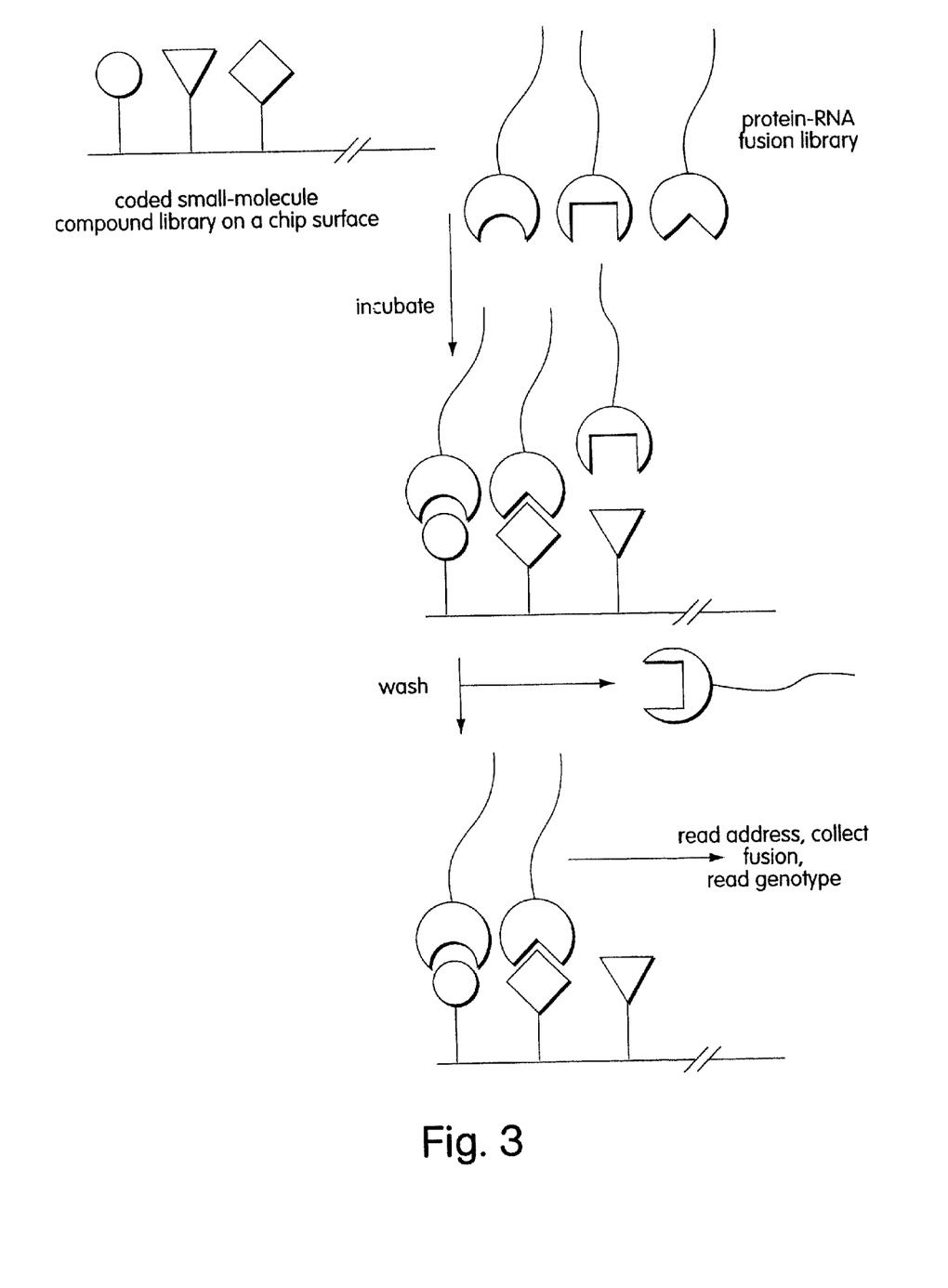
FIG. 3 is a schematic illustration of an exemplary approach to screening an addressable array of compounds immobilized on a microchip with a library of protein-nucleic acid fusions.

Alternatively, multiple compounds may be screened simultaneously against multiple protein-nucleic acid fusions. Two exemplary formats for carrying out this type of screen are shown in FIGS. 2 and 3. In these formats, an encoded (addressable) library of small molecules is immobilized on beads or any other surface, such as a chip. The solid phase-bound library is then incubated with screening buffer containing BSA or another inert protein to reduce non-specific binding. Subsequently, the buffer solution is drained, and the small molecule compound library is incubated with a fusion library, followed by washes with screening buffer to remove non-specifically bound molecules. Protein-nucleic acid fusion molecules specifically binding to small molecules are then detected or, if a bead format is utilized, sorted and collected. A reading code (or tag or address) is used to identify the small molecule compound, and reading of the nucleic acid portion of bound fusion molecules is used to identify the protein (as described below).

Protein-nucleic acid fusion molecules of different genotypes and different phenotypes can sometimes bind to the same small molecule compound. If desired, therefore, the bound fraction of fusion molecules may be collected, amplified, and reincubated with an identified ligand under more stringent conditions (e.g., a lower concentration of protein-nucleic acid fusion). This process may be repeated any number of times, allowing for the isolation of a receptor with any desired ligand affinity (for example, selection for a receptor having the highest affinity).

In addition, once identified, a binding interaction between a solid phase-bound compound and a fusion molecule may be confirmed or analyzed by addition of free ligand or free protein to a compound-fusion complex in a standard binding assay.

The present screens may be used to identify unknown compound-protein interactions or may be exploited in circumstances where some general knowledge of an interaction (for example, between a ligand and a receptor) is available. In the latter case, biased libraries may be used for screening. Such libraries may contain particular classes of compounds (or proteins) or modifications of a single compound (or protein). In general, the biasing element tends to increase the average affinity of a ligand for a target receptor and to orient the ligand in a uniform way (see, for example, Chen et al., JACS (1993) vol. 115, p. 12591–12592). This type of approach facilitates the identification, for example, of ligands which bind to a receptor at a targeted site.

Preparation of Protein-Nucleic Acid Fusions

As discussed above, the present techniques may be applied to any population of protein-nucleic acid fusions, including protein-RNA fusions, protein-DNA fusions, and fusions between proteins and hybrid DNA-RNA molecules.

For use in the methods described herein, random libraries of protein-RNA fusion molecules may be prepared, for example, as described in Szostak et al., Selection of Proteins Using RNA-Protein Fusions, U.S. Ser. No. 09/007,005, Jan. 14, 1998, now U.S. Pat. No. 6,258,558 B1, and U.S. Ser. No. 09/247,190, Feb. 9, 1999, now U.S. Pat. No. 6,261,804 B1; Roberts & Szostak, Proc. Natl. Acad. Sci. USA (1997) vol. 94, p. 12297–12302; or Kuimelis et al., Addressable Protein Arrays, U.S. Ser. No. 60/080,686, Apr. 3, 1998, now abandoned, and U.S. Ser. No. 09/282,734, Mar. 31, 1999). Alternatively, libraries of cellular RNA-protein fusion molecules may be prepared from mRNAs or cDNAs that lack 3'-untranslated regions, for example, as described in Lipovsek et al. (Methods for Optimizing Cellular RNA-Protein Fusion Formation, U.S. Ser. No. 60/096,818, Aug. 17, 1998, now abandoned) and Hammond (Methods for Producing Nucleic Acids Lacking 3'-Untranslated Regions and Optimizing Cellular RNA-Protein Fusion Formation, U.S. Ser. No. 09/374,962, Aug. 16, 1999, now U.S. Pat. No. 6,312,927).

To label such protein-RNA fusions, any standard labeling method and any detectable label (including, for example, radioactive, fluorescent, and chemiluminescent labels) may be utilized. If desired, fusions may be radioactively labeled by generating the fusion or fusion components in the presence of radioactive amino acids (for example, $^{35}$S- or $^{14}$C-labeled amino acids) or radioactive nucleotides (for example, $^{35}$S- or $^{32}$P-labeled nucleotides). Alternatively, fusion molecules may be fluorescently labeled. In one particular example, the DNA linker (for example, the $dA_{27}dCdCP$ linker described in Roberts & Szostak, Proc. Natl. Acad. Sci. USA (1997) vol. 94, p. 12297–12302) may be modified with a fluorescein phosphoramidite marker (Glen Research, Sterling, Va.), and this linker used for the synthesis of fluorescent protein-RNA fusions. In yet another alternative, protein-RNA fusions prepared according to the method of Roberts & Szostak (Proc. Natl. Acad. Sci. USA (1997) vol. 94, p. 12297–12302; and Selection of Proteins Using RNA-Protein Fusions, U.S. Ser. No. 09/007,005, Jan. 14, 1998, now U.S. Pat. No. 6,258,558 B1, and U.S. Ser. No. 09/247,190, Feb. 9, 1999, now U.S. Pat. No. 6,261,804 B1) or cellular RNA-protein fusions prepared according to the method of Lipovsek et al. (Methods for Optimizing Cellular RNA-Protein Fusion Formation, U.S. Ser. No. 60/096,818, Aug. 17, 1998, now abandoned) or Hammond (Methods for Producing Nucleic Acids Lacking 3'-Untranslated Regions and Optimizing Cellular RNA-Protein Fusion Formation, U.S. Ser. No. 09/374,962, Aug. 16,1999, now U.S. Pat. No. 6,312,927) may be labeled by base pairing the fusion to a fluorescently-labeled oligonucleotide (for example, base pairing a fluorescent poly-dT oligonucleotide to the $dA_{27}dCdCP$ linker).

Alternatively, protein-DNA fusions may also be labeled using similar techniques. Such protein-DNA fusions may be generated as described, for example, in Lohse et al., DNA-Protein Fusions and Uses Thereof, U.S. Ser. No. 60/110,549, Dec. 2, 1998, now abandoned and incorporated into U.S. Ser. No. 09/453,190, Dec. 2, 1999). In yet another alternative, the above labeling techniques may be used for fusions of proteins to hybrid DNA-RNA portions (i.e., one strand of each). Such hybrid fusions are generated, for example, by subjecting a RNA-protein fusion to a step of reverse transcription using standard techniques.

Preparation of Compounds

For carrying out the screening methods of the invention, any compound library may be utilized. Such libraries may be derived from natural products, synthetic (or semi-synthetic) extracts, or chemical libraries according to methods known in the art. Those skilled in the field of drug discovery and development will understand that the precise source of compounds is not critical to the screening procedure(s) of the invention. Examples of natural compound sources include, but are not limited to, plant, fungal, prokaryotic, or animal sources, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries may be obtained commercially or may be produced according to methods known in the art. Furthermore, if desired, any library or compound is readily modified using standard chemical, physical, or biochemical methods.

In certain methods of the invention, interacting compounds are identified as a result of a detectable label, or "tag," bound to either the compound or its associated solid support (for example, bead). A coded library of small molecule compounds may be prepared on beads as described, for example, in Combs et al., JACS (1996) Vol. 118, p. 287–288. In addition, a number of encoding schemes are available, including peptide and nucleic acid codes (Kerr et al., JACS (1993) vol. 115, p. 2529–2531; and Brenner & Lerner, Proc. Natl. Acad. Sci. USA (1992) vol. 89, p. 5381–5383); chemical tags (Ohlmeyer et al., Proc. Natl. Acad. Sci. USA (1993) vol. 90, p. 109222–10926; and Maclean et al., Proc. Natl. Acad. Sci. USA (1997) vol. 94, p. 2805–2810); fluorophore tags (Yamashita & Weinstock (SmithKline Beecham Corporation), WO95/32425 (1995); and Sebestyen et al., Pept. Proc. Eur. Pept. Symp. 22nd 1992 (1993), p. 63–64); and radio frequency tags (Nicolaou et al., Angew. Chem. Int. Ed. Engl. (1995) vol. 34, p. 2289–2291; and Moran et al., JACS (1995) vol. 117, p. 10787–10788). Such labels may be read as described in the references above.

Alternatively, an addressable library of compounds (for example, small molecule compounds) may be prepared on a solid surface, such as a chip surface. A variety of techniques are available for immobilizing compounds on a chip surface, and any may be utilized. Preferable techniques include photolithography (Affymetrix, Santa Clara, Calif.), mechanical microspotting (Schena et al., Science (1995) vol. 270, p. 467–470; Synteni, Fremont, Calif.) and ink jetting (Incyte Pharmaceuticals, Palo Alto, Calif.; and Protogene, Palo Alto, Calif.).

Identification of Compound-Fusion Interactions

To identify interactions between compounds (for example, coded compounds) and protein-nucleic acid fusions, any method may be utilized which provides a means for detecting a label associated with the compound or fusion or, if appropriate, for isolating and determining the identity or "address" of the compound-fusion pair.

In one particular example, compound-protein pairs (for example, small molecule-protein pairs) may be isolated and identified on beads. To detect a label associated with a bead, the bead resin is preferably plated out, followed by scanning, for example, for a fluorescent or radioactive label (using, for example, a Phosphorimager to detect a radioactive label). Protein-nucleic acid fusion molecules binding to small molecules presented on a bead may be isolated by physically sorting the beads. Alternatively, beads bound to fluorescently labeled fusion molecules may be sorted on a fluorescence activated cell sorter (FACS). Selected beads may be individually and spatially separated (for example, into the wells of a 96-well microtiter plate). For RNA-protein fusions, molecules bound to individual beads may then be identified by reverse transcription of the RNA portion, followed by sequencing of the DNA as described by Roberts & Szostak (Proc. Natl. Acad. Sci. USA (1997) vol. 94, p. 12297–12302) and Szostak et al. (Selection of Proteins Using RNA-Protein Fusions, U.S. Ser. No. 09/007,005, Jan. 14, 1998, now U.S. Pat. No. 6,258,558 B1, and U.S. Ser. No. 09/247,190, Feb. 9, 1999, now U.S. Pat. No. 6,261,804 B1). The tag coding for the compound (for example, the small molecule compound) on each individual bead may be read as described above.

Alternatively, ligand-receptor pairs on a chip surface may be detected by scanning the chip surface for radioactivity or fluorescence. The address of the interacting pair on the chip reveals the identity of the compound (for example, the small molecule compound). The fusion molecule may be picked from the chip surface using an addressable microcollector or any other standard method (see, for example, Kuimelis et al., Addressable Protein Arrays, U.S. Ser. No. 60/080,686, Apr. 3, 1998, now abandoned, and U.S. Ser. No. 09/282,734, Mar. 31, 1999). The retrieved fusion molecule may then be identified by characterizing the nucleic acid portion of the fusion as described above.

Compound Screening Utilizing a Bead Format

As described above, compounds may be immobilized on a bead solid support and used to screen for protein-nucleic acid fusions, and specifically for RNA-protein fusions, which are capable of interacting with the compound. In one particular working example of this approach, the dihydrofolate reductase (DHFR) gene was cloned out of a human liver cDNA library (Maxim Biotech, South San Francisco, Calif.). The construct contained the entire DHFR gene with an added C-terminal DYKDDDDK-ASA peptide tag (SEQ ID NO: 1). RNA-protein fusions of DHFR were prepared by PCR amplification of the DHFR coding sequence followed by fusion formation as described in Roberts & Szostak (Proc. Natl. Acad. Sci. USA (1997) vol. 94, p. 12297–12302) and Szostak et al. (Selection of Proteins Using RNA-Protein Fusions, U.S. Ser. No. 09/007,005, Jan. 14, 1998, now U.S. Pat. No. 6,258,558 B1, and U.S. Ser. No. 09/247,190, Feb. 9, 1999, now U.S. Pat. No. 6,261,804 B1). The fusions were purified using oligo-dT-cellulose affinity chromatography (Edmonds et al., Proc. Natl. Acad. Sci. USA (1971) vol. 68:1336) and reverse transcribed with Superscript II reverse transcriptase according to the manufacturer's instructions. 100 fmol of DHFR fusion in 10 μL 1× buffer (Phosphate buffered saline, 1 M NaCl, 1 mg/ml BSA, 0.1 mg/ml sheared DNA, 1% v/v Triton X-100) was combined with 10 μL pre-equilibrated methotrexate-agarose (as described in Kaufman, Methods Enzymol. (1974) vol. 34:272–81) in a 500 μL eppendorf tube. The slurry was incubated for 30 minutes at ambient temperature with mixing every 5 minutes. The slurry was then centrifuged for 1 minute at 3000 rpm in an eppendorf microfuge. The liquid was removed, and the methotrexate-agarose was washed 3 times with 500 μL of 1× buffer. The fusions were then eluted by incubation of the methotrexate-agarose in 50 μL 30 μM methotrexate for 30 minutes at 37° C.

Figure 4:
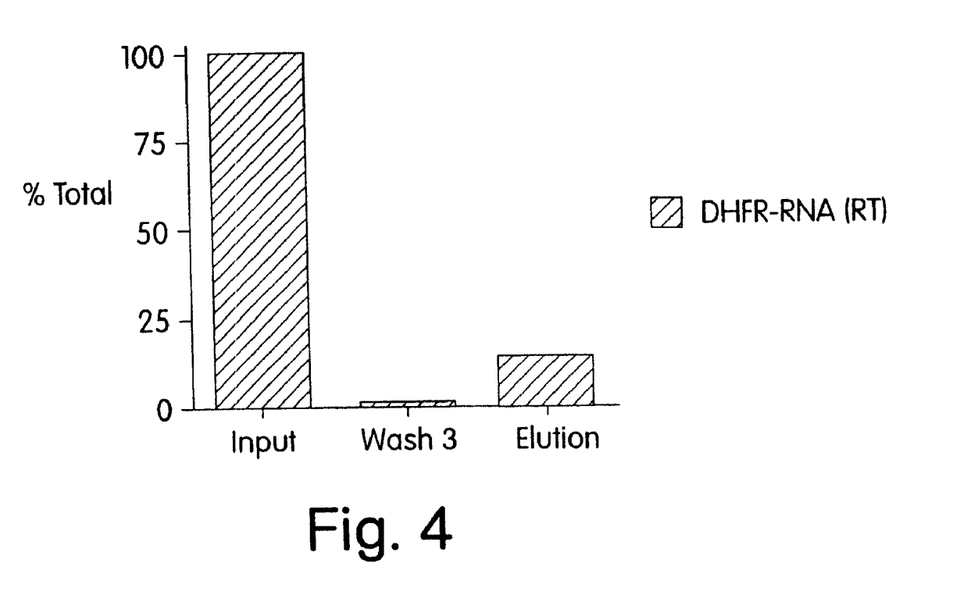
FIG. 4 is a graph illustrating compound binding to an RNA-protein fusion on a bead solid support.

The results of this interaction assay are shown in FIG. 4. In this figure, the percent of total fusion molecules was monitored by measuring $^{35}$S-methionine label incorporated into the fusions during the translation step. As indicated, the third wash contained no significant amount of fusion molecules. In addition, of the total amount of fusion included within the matrix, 86% flowed through the bead column, and the other 14% was efficiently eluted with methotrexate.

Use

The present methods provide an efficient means for screening either small or large libraries for compound-protein binding interactions. In addition, these methods may be utilized to screen protein-nucleic acid fusions against one compound or against a library of compounds.

Commercial uses for screening a library of fusion molecules against a single compound include, without limitation, identification of a protein binder for a desired small molecule from a random pool of fusion molecules, rationalization of the mechanism of action of a given drug by isolating the cellular target from a pool of cellular mRNA-protein fusion molecules (or a pool of the DNA-protein fusion or hybrid fusion derivatives), and rationalization of the side effect profile of a given drug by isolating most or all target proteins from a pool of cellular mRNA-protein (or, DNA-protein or hybrid-protein) fusion molecules, leading to an improved drug with reduced side effects.

Uses for screening a library of fusion molecules against an encoded (addressable) library of compounds include, without limitation, screening a library of small molecule

SEQUENCE LISTING

<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Synthetic affinity tag

<400> SEQUENCE: 1

Asp Tyr Lys Asp Asp Asp Asp Lys Ala Ser Ala
1               5                   10 compounds with a library of nucleic acid-protein (for example, cellular mRNA-protein) fusion molecules for potential new lead compounds (for example, ligands or enzyme inhibitors), screening a library of nucleic acid-protein (for example, cellular mRNA-protein) fusion molecules with a library of small molecule compounds for potential targets (for example, receptors or enzymes), and mapping of binding interactions between the members of a protein library and the members of a small molecule compound library, thus providing a catalogue of ligand-protein pairs.

All patents and publications mentioned herein are hereby incorporated by reference.

Other embodiments are within the claims.

What is claimed is:

1. A method for detecting interactions between one or more compounds and one or more protein-nucleic acid fusions, said method comprising:
   (a) providing a compound library which comprises a plurality of different compounds, wherein said compounds are immobilized on a solid support;
   (b) simultaneously contacting said different immobilized compounds in a single reaction chamber with a protein-nucleic acid fusion library which comprises a plurality of different protein-nucleic acid fusions under conditions which allow the formation of one or more compound-fusion complexes;
   (c) isolating said one or more immobilized compound-fusion complexes from unbound protein-nucleic acid fusions; and
   (d) detecting said one or more compound-fusion complexes as an indication that one or more protein-nucleic acid fusions interact with one or more compounds.

2. The method of claim 1, wherein said protein-nucleic acid fusions are protein-RNA fusions.

3. The method of claim 1, wherein said protein-nucleic acid fusions are protein-DNA fusions.

4. The method of claim 1, wherein said protein-nucleic acid fusions are proteins fused to DNA-RNA hybrid molecules.

5. The method of claim 1, wherein said solid support is a chip and said compound library is immobilized on said chip in an addressable array.

6. The method of claim 5, wherein each member of said protein-nucleic acid fusion library is detectably labeled.

7. The method of claim 1, wherein the step of detecting further comprises recovering said compound-fusion complexes, or the components thereof, by release from said solid support.

8. The method of claim 1, wherein said method further comprises, before or after said detecting step (d), recovering said one or more protein-nucleic acid fusions from said solid support and identifying the protein portion.

9. The method of claim 8, wherein the identity of said protein portion is determined from the sequence of the nucleic acid portion of said one or more protein-nucleic acid fusions.

10. The method of claim 1, wherein said compounds are small molecules.

11. A method for detecting interactions between one or more compounds and one or more protein-nucleic acid fusions, said method comprising:
   (a) providing a compound library which comprises a plurality of different compounds, wherein said compounds are immobilized on a solid support;
   (b) simultaneously contacting said library of different immobilized compounds with a protein-nucleic acid fusion library which comprises a plurality of different protein-nucleic acid fusions under conditions which allow said protein-nucleic acid fusions to bind to said compounds; and
   (c) detecting one or more bound protein-nucleic acid fusions as an indication that one or more protein-nucleic acid fusions interact with one or more compounds of said compound library.

12. The method of claim 11, wherein said protein-nucleic acid fusions are protein-RNA fusions.

13. The method of claim 11, wherein said protein-nucleic acid fusions are protein-DNA fusions.

14. The method of claim 11, wherein said protein-nucleic acid fusions are proteins-fused to DNA-RNA hybrid molecules.

15. The method of claim 11, wherein said protein-nucleic acid fusions are detectably labeled and said interactions are indicated by the association of the detectable label with said solid support.

16. A The method of claim 11, wherein, before or after said detecting step (c), said one or more bound protein-nucleic acid fusions are recovered by release from said solid support.

17. The method of claim 11, wherein, before or after said detecting step (c), said method further comprises recovering said one or more protein-nucleic acid fusions from said solid support and identifying said protein portion.

18. The method of claim 17, wherein the identity of said protein portion is determined from the sequence of the nucleic acid portion of said one or more protein-nucleic acid fusions.

19. The method of claim 11, wherein said solid support is a column, glass slide, chip, or bead.

20. The method of claim 11, wherein said compounds are small molecules.

21. A method for detecting interactions between one or more compounds and one or more protein-nucleic acid fusions, said method comprising:
   (a) providing a compound library which comprises a plurality of compounds, wherein said compounds are immobilized on a plurality of support elements;
   (b) contacting said immobilized compounds in a single reaction chamber with a protein-nucleic acid fusion library which comprises a plurality of protein-nucleic acid fusions under conditions which allow the formation of one or more compound-fusion complexes;
   (c) sorting said one or more immobilized compound-fusion complexes on said support elements; and
   (d) detecting said one or more compound-fusion complexes as an indication that one or more protein-nucleic acid fusions interact with one or more compounds of said compound library.

22. The method of claim 21, wherein said protein-nucleic acid fusions are protein-RNA fusions.

23. The method of claim 21, wherein said protein-nucleic acid fusions are protein-DNA fusions.

24. The method of claim 21, wherein said protein-nucleic acid fusions are proteins fused to DNA-RNA hybrid molecules.

25. The method of claim 21, wherein each of said support elements is a bead.

26. The method of claim 25, wherein each said bead is coded with a unique detectable label.

27. The method of claim 26, further comprising, before or after said detecting step (d), identifying the compounds of said one or more fusion complexes by said unique detectable label associated with said bead.

28. The method of claim 26, wherein said detectable label is selected from the group consisting of a peptide label, a nucleic acid label, a chemical label, a fluorescent label, and a radio frequency tag.

29. The method of claim 21, wherein the step of detecting further comprises recovering said compound-fusion complexes, or the components thereof, by release from said support elements.

30. The method of claim 21, wherein said method further comprises, before or after said detecting step (d), recovering the one or more protein-nucleic acid fusions from said support elements and identifying said protein portion.

31. The method of claim 30, wherein the identity of said protein portion is determined from the sequence of the nucleic acid portion of said one or more protein-nucleic acid fusions.

32. The method of claim 21, wherein said compounds are small molecules.

* * * * *